US00PP08594P

United States Patent [19]

Warriner, deceased

[11] Patent Number: Plant 8,594

[45] Date of Patent: Feb. 15, 1994

[54] HYBRID TEA ROSE PLANT NAMED 'JACPEND'

[75] Inventor: William A. Warriner, deceased, late of Tustin, Calif., by Alene B. Warriner, legal representative

[73] Assignee: Bear Creek Gardens, Inc., Medford, Oreg.

[21] Appl. No.: 953,978

[22] Filed: Sep. 28, 1992

[51] Int. Cl.[5] ..... A01H 5/00

[52] U.S. Cl. ..... Plt./18

[58] Field of Search ..... Plt. 11, 18, 19, 20, Plt. 12

*Primary Examiner*—Howard J. Locker

*Attorney, Agent, or Firm*—Klarquist, Sparkman, Campbell, Leigh and Whinston

[57] ABSTRACT

A hybrid tea class rose plant having a vigorous, upright habit of growth; large, well-formed flowers; a moderate scent, and a color and petal count intermediate between its parents.

1 Drawing Sheet

The present invention relates to a new and distinct variety of rose plant of the hybrid tea class which was originated by the inventor by crossing the variety JACpico, U.S. Plant Pat. No. 3997, with the variety JACtop, U.S. Plant Pat. No. 6,092.

The primary objective of this breeding was to produce a new rose variety having the excellent flower form and robust growth of JACpico combined with the larger open flowers and higher petal count of JACtop. The objective was substantially achieved along with other desirable improvements as evidenced by the following unique combination of characteristics which are outstanding in the new variety and which distinguish it from its parents, as well as from all other varieties of which I am aware:

1. Large well-formed flowers;
2. Vigorous upright growth;
3. Moderate scent;
4. A color and petal count intermediate between its parents.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Horticultural Society (London) Colour Chart, except where ordinary dictionary significance of color is indicated.

Parentage:

*Seed parent.*—JACpico, U.S. Plant Pat. No. 3,997.

*Pollen parent.*—JACtop, U.S. Plant Pat. No. 6,092.

Classification:

*Botanical.*—*Rosa hybrida.*

*Commercial.*—Hybrid tea.

FLOWER

Observations made from specimens grown in a garden environment in Somis, Calif., from March through June, 1992.

Blooming habit: Recurrent.

Bud:

*Size.*—1½ to 1¾ inches when the petals start to unfurl.

*Form.*—Long, pointed ovoid.

*Color.*—When sepals first divide, bud color is Red Group 40D. When half blown, the upper sides of the petals are Red Group 48C with petal edges darker at Red Group 48B; and the lower sides of the petals are Red Group 48C with petal edges darker at Red Group 48B.

*Sepals.*—Color: Green Group 138B. Surface texture: Covered with fine hairs. There aree three lightly appendaged sepals. There are two unappendaged sepals with hairy edges.

*Receptacle.*—Color: Green Group 138B. Shape: Apple. Size: Broad. Surface: Smooth.

*Peduncle.*—Length: Medium. Surface: Smooth. Color: Bronzy. Strength: Stiff, erect.

Bloom:

*Size.*—Large. Average open size is 5 inches.

*Borne.*—Singly.

*Stems.*—Long (16 to 20 inches), strong.

*Form.*—When first open: High centered. Permanence: Retains its form to the end, outer petals curl back.

*Petalage.*—Number of petals under normal conditions: 25-30.

*Color.*—The upper and reverse sides of the petals are Red Group 48C with some darkening on the petal edges to Red Group 48B. The bases of the petals have a small pale yellow half moon (¼×¼ inch) at the point of attachment. The major color on the upper side is Red Group 48C.

*Variegations.*—None.

*Discoloration.*—The general tonality at the end of the first day: No change. At the end of the third day: No change.

*Fragrance.*—Moderate.

Petals:

*Texture.*—Thick, leathery.

*Shape.*—Round.

*Form.*—Tips slightly recurved, edges slightly quilled.

*Arrangement.*—Imbricated, with no petaloids in the center.

*Persistence.*—Drop off cleanly.

*Lastingness.*—On the plant: Long, 5 days. As a cut flower: Long, 7 days.

Reproductive parts:

*Anthers.*—Size: Medium. Quantity: Many. Color: Yellow. Arrangement: Regular around the styles.

*Filaments.*—Color: Reddish brown.

*Pollen.*—Color: Lemon yellow.

*Styles.*—Color: Red.

*Stigmas.*—Color: Greenish white.

Form: Bush.

Growth: Very Vigorous, upright and branching.

Foliage:

*Number of leaflets on normal mid-stem leaves.*—5.

*Size.*—Large.

*Quantity.*—Abundant.

*Color.*—New foliage: Reddish. Old foliage: Dark green, semi-glossy.

Leaflets:

*Shape.*—Broadly oval.

*Texture.*—Upper side: Leathery, semi-glossy.

*Edge.*—Serrated.

*Serration.*—Single, small.

*Petiole rachis.*—Color: Reddish.

*Petiole underside.*—Smooth with occasional prickles.

*Stipules.*—Medium and bearded.

*Disease resistance.*—Susceptible to mildew but resistant to rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base and on laterals from main canes: Many.

*Form.*—Medium, hooked downward.

*Color when young.*—Green.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its vigorous upright habit of growth, its large, well-formed flowers, its moderate scent and a color and petal count intermediate between its parents.

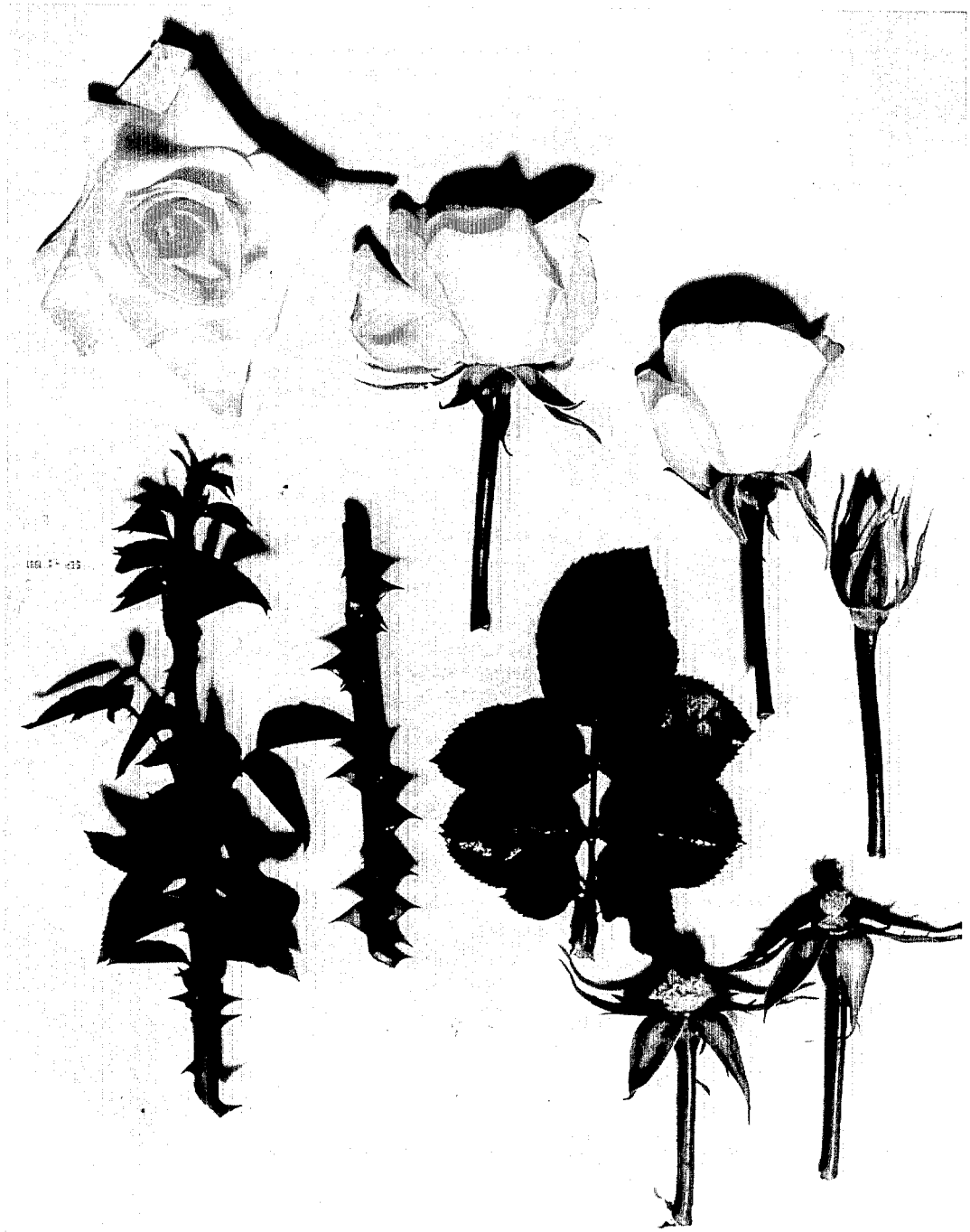

* * * * *